United States Patent [19]

Abelentsev et al.

[11] Patent Number: 4,992,667
[45] Date of Patent: Feb. 12, 1991

[54] DEVICE FOR MEASURING MOISTURE CONTENT OF SOIL AND SNOW WATER STORAGE

[76] Inventors: Vladimir V. Abelentsev, ulitsa Solnechnaya, 31; Evgeny V. Kolomeets, prospekt Al-Farabi, 67, kv. 9; Vladimir V. Oskomov, ulitsa Baumana, 242, kv. 73; Vladimir N. Sevostyanov, prospekt Lenina, 192B, all of, Alma-Ata; Shepa D. Fridman, Zheleznodorozhny, ulitsa Smelchaka, 7, kv. 64, Moskovskaya oblast, all of U.S.S.R.

[21] Appl. No.: 347,510

[22] Filed: May 4, 1989

[51] Int. Cl.$^5$ ............................................. G01N 23/09
[52] U.S. Cl. .............................. 250/390.05; 250/358.1
[58] Field of Search ..................... 250/390.05, 390.06, 250/358.1

[56] References Cited

U.S. PATENT DOCUMENTS 4,047,042  9/1977  Wada et al. ..................... 250/390.06

OTHER PUBLICATIONS

A. V. Dmitriev, Sh. D. Friedman. Fundamentals of Remote Methods for Measuring Snow Water Storage and Moisture Content of Soils, 1979, Gidrometeoizat Pub., Leningrad, pp. 281, 288.
E. V. Kolomeets, Sh. D. Fridman, Method for Determining Snow Water Storage and Soil Moisture, 1981, Gidrometeoizdat Pub., Leningrad, p. 3.

Primary Examiner—Carolyn E. Fields
Attorney, Agent, or Firm—Lilling and Lilling

[57] ABSTRACT

A device for measuring moisture content of soil and snow water storage has a first detector of cosmic neutrons passed through the soil placed deep in the soil at a pre-set depth, a second cosmic-ray neutron detector placed above the soil at an altitude which is greater than maximum snow pack thickness or vegetation layer height and spaced from the first neutron detector at a distance which is not greater than the path length of thermal neutrons in the atmosphere, and a soil background gamma-quantum radiation detector placed on the soil surface and spaced from the first neutron detector at a distance which is not greater than the gamma-quantum path length in the soil. Outputs of the neutron detectors and gamma-quantum radiation detector, are coupled to a respective series circuit, including a unit for detecting pulses of a predetermined amplitude, a pulse counter to which is connected a timer, and a recorder.

4 Claims, 5 Drawing Sheets

DEVICE FOR MEASURING MOISTURE CONTENT OF SOIL AND SNOW WATER STORAGE

FIELD OF THE INVENTION

The invention relates to devices for measuring moisture content, and more specifically it deals with a device for measuring moisture content of soil and snow water storage.

The invention may be successfully used in agriculture, hydrology and agrometeorology for determining snow pack water storage in mountains for evaluating runoff of mountain rivers, and for determining moisture content of soil at various depths for evaluation of ground water level and schedule and volumes of reclamation operations. It may also be used in glaciology and hydrometeorology.

BACKGROUND OF THE INVENTION

Practical importance of information on storage, and dynamics of accumulation of snow on large territories and information of moisture content of soils is enormous. In this light, the main requirements imposed upon devices for measuring moisture content of soil and snow water storage are high accuracy of measurement, especially of soil moisture content measurement, and the possibility of continuous measurement so as to monitor dynamics of the process of variation of soil moisture content and snow water storage.

Widely known contact methods are most popular in measuring soil moisture content and snow water storage. Thus, snow scales for determining the geometrical thickness of snow pack and standard snow samplers that make it possible to sample snow and determine its density are used for measuring snow water storage. A weighing method is used for measuring moisture content of soil, which requires soil sampling and dehydrating. Standard burets are used for sampling, and samples are dehydrated in drying cabinets. These methods are labour consuming; they can be associated with a risk of life when meassurements are carried out in mountains, and cannot ensure the desired accuracy of measurements since, e.g. in measuring density of thawing snow, a part of the moisture is not measured by the densimeter. In addition, when soil moisture content is measured, it is impossible to obtain trustworthy results for large monitored areas using small-volume soil samples.

Methods using devices for remote measurement of soil moisture content and snow water storage are used concurrently with the contact methods. Such measurements enable automation of the measurement process and do not require sampling so that structure of the medium and processes occurring therein, such as snow accumulation, thawing and wetting are not affected. These measurements are based on recording electromagnetic radiations of both natural and artificial origin within a broad range of wavelengths from centimetric waves to gamma-radiation at the wavelength of $10^{-11}$ cm, including the areas of visible, ultraviolet and infrared radiation (E. V. Kolomeets, Sh. D. Fridman. Method for Determining Snow Water Storage and Soil Moisture Content By Detecting Cosmic Rays. (in Russian), 1981. Gidrometeoizdat Publishing House, Leningrad. p.3). A device for measuring moisture content of soil and snow water storage using penetrating electromagnetic radiation in a predetermined wavelength range comprises a detector of electromagnetic radiation connected to a recorder. Moisture content of soil and snow water storage are determined by a change in electromagnetic radiation which depends on soil moisture content and snow water storage values.

Aerial gamma-survey is most widely used for determining moisture content of soil and snow water storage (A. V. Dmitriev, Sh. D. Fridman. Fundamentals of Remote Methods for Measuring Snow Water Storage and Moisture Content of Soils Using Gamma-Radiation of the Earth (in Russian), 1979. Gidrometeoizdat Publishing House, Leningrad. pp.281; 288). A device for carrying out aerial gamma-survey comprises a detector of background gamma-radiation from the snow or soil surface mounted on board an aircraft which is used for repeatedly measuring gamma-radiation. Soil moisture content and snow water storage are evaluated by attenuation of gamma-radiation.

Devices for measuring soil moisture content and snow water storage making use of penetrating natural origin electromagnetic radiation cannot ensure simultaneous and independent measurement of soil moisture content and snow water storage, nor do they ensure the desired accuracy since soil humus and biomass of the vegetation layer influence the measurements.

Devices with artificial sources of penetrating radiation are used for measuring soil moisture content and snow water storage (E. V. Kolomeets, Sh.D. Fridman. Method for Determining Snow Water Storage and Soil Moisture Content Using Cosmic Rays (in Russian). 1981. Gidrometeoizdat Publishing House, Leningrad. p. 74). Thus, in a device for measuring moisture content of soil, use is made of an isotope neutron source, and a device for measuring snow water storage incorporates an isotope gamma-radiation source, and appropriate detectors are used in these devices. Moisture content of soil and snow water storage may be determined by the character of a change in the artificial radiation that passed through the body of snow or soil.

The employment of isotope sources results in certain difficulties in that it is necessary to provide biological protection, and it can bring about pollution of the environment. The greater the water storage being measured, the higher is the capacity of the isotope source; alternativly, the device should have several isotope sources and detectors placed at different altitudes. In addition, these devices cannot ensure the desired accuracy of measurement because of the influence of soil humus and biomass of a vegetation layer, especially in a wide measurement range, and one and the same device cannot be used for measuring both soil moisture content and snow water storage.

Known in the art is a device for measuring moisture content of soil and snow water storage, comprising a first detector of cosmic-ray neutrons that passed through the soil placed deep in the soil at a pre-set depth and a second detector of cosmic-ray neutrons placed above the soil at an altitude which is greater than maximum thickness of snow pack or height of vegetation layer and which is spaced from the first detector of cosmic-ray neutrons at a distance which does not exceed the path length of thermal neutrons before absorption in the atmosphere, each detector being electrically coupled to a respective series circuit including a unit for detecting pulses of a predetermined amplitude and a pulse counter having a control input to which is connected a timer having an output connected to a recorder (E.V. Kolomeets, Sh. D. Fridman. Method for Determining Snow Water Storage and Soil Moisture Content Using Cosmic Rays (in Russian), 1981, Gidrometeoizdat Publishing House, Leningrad. pp. 59;83;84).

This device makes it possible to carry out simultaneous measurement of soil moisture content and snow water storage, provided only that one of the measured values remains unchanged. Consequently, this device cannot ensure the desired accuracy of measurement as the values being measured change with time and are interlinked. Moreover, measurements accuracy is influenced by soil humus and biomass of a vegetation layer which are not taken into account during measurements.

SUMMARY OF THE INVENTION

One object of the invention is to provide a device for measuring moisture content of soil and snow water storage which enhances accuracy of independent measurement of moisture content of soil and snow water storage.

Another object of the invention is to provide a device for measuring moisture content of soil which is capable of simultaneously carrying out measurement of soil moisture content and snow water storage with high accuracy.

The above objects are accomplished by a device for measuring moisture content of soil and snow water storage, comprising a first detector of cosmic-ray neutrons passed through the soil placed deep in the soil at a pre-set depth, and a second cosmic-ray neutron detector placed above the soil at an altitude which is greater than maximum snow pack or vegetation layer height and spaced from the first cosmic-ray neutron detector at a distance which is not greater than the path length thermal neutrons before absorption in the atmosphere, each detector being electrically coupled to a respective series circuit including a unit for detecting pulses of a predetermined amplitude and a pulse counter having a control input to which is connected a timer and an output connected to a recorder. According to the invention, a soil background gamma-quantum radiation is placed on the soil surface and spaced from the first cosmic-ray neutron detector at a distance which is not greater than the gamma-quantum path length before absorption in the soil, an auxiliary unit for detecting pulses of a predetermined amplitude is connected to the soil background gamma-quantum radiation detector, an auxiliary pulse counter has an input connected to an output of the auxiliary unit for detecting pulses of a predetermined amplitude, an auxiliary timer is connected to a control input of the auxiliary pulse counter, and an auxiliary recorder is connected to an output of the auxiliary pulse counter.

The device for measuring moisture content of soil in the presence of snow pack on the soil preferably comprises an auxiliary detector of cosmic-ray neutrons passed through the soil having a base made of a hydrogen-containing material, the base being placed on the soil surface and spaced from the first and second cosmic-ray neutron detectors at a distance which is not greater than the path length of thermal neutrons before absorption in the atmosphere; an auxiliary vegetation layer background gamma-quantum radiation detector placed on the soil surface and spaced from the auxiliary cosmic-ray neutron detector at a distance which is not greater than the gamma-quantum path length before absorption in the vegetation layer; two more auxiliary units for detecting pulses of a predetermined amplitude of which one is electrically coupled to the auxiliary cosmic-ray neutron detector and the other is electrically coupled to the auxiliary vegetation layer background gamma-quantum radiation detector; two auxiliary pulse counters, each having an input connected to an output of the respective auxiliary unit for detecting pulses of a predetermined amplitude; two auxiliary timers, each being connected to a control input of the respective auxiliary pulse counter; and two auxiliary recorders, each being connected to an output of the respective auxiliary pulse counter. It is expedient that the device for measuring the moisture content of soil is provided with the following units connected in series: a divider producing output electric signals corresponding to the relative intensity of the cosmic-ray neutrons passed through the soil and snow layer and background gamma-quantum radiation from the soil and vegetation layer, the inputs of said divider being connected to the outputs of the pulse counters and a nonlinear converter converting the electric signals corresponding to the relative intensities of the cosmic-ray neutrons passed through the soil and snow layer and the background gamma-quantum radiation from the soil and vegetation layer corresponding to the soil moisture and water storage of snow. The recorders are united into a common recorder, the outputs of said nonlinear electric signals are connected to the inputs of the common recorder.

It is reasonable, when in the device for measuring the moisture content of soil, the nonlinear converter, converting the electric signals corresponding to the relative intensities of the cosmic-ray neutrons passed through the soil and snow layer and the background gamma-quantum radiation from the soil and vegetation layer into electric signals corresponding to the water content of soil and the water storage of snow, comprises a first memory unit storing calibration dependence of the cosmic-ray radiation intensity passed through the soil; the input of the memory unit receives an electric signal corresponding to the relative intensity of the background gamma-quantum radiation; a first multiplier having one input connected to the output of the first memory unit and having another input receiving an electric signal corresponding to the relative intensity of the cosmic-ray neutrons passed through the soil; a second memory unit storing calibration dependence of the intensity of the comsic-ray neutrons passed through the vegetation layer on the biomass thereof, said second memory unit having an input receiving an electric signal corresponding to the relative intensity of the vegetation layer background gamma-quantum radiation; a second multiplier having one input connected to the output of the second memory unit and having another input receiving an electric signal corresponding to the cosmic-ray neutrons passed through the snow layer; a third memory unit storing calibration dependence of the humus-corrected intensity of the cosmic-ray neutrons passed through the soil on the soil moisture content, the input of said third memory unit being connected to the output of the first multiplier; and a fourth memory unit storing calibration dependence of the humus-corrected relative intensity of the cosmic-ray neutron passed through the snow layer on the water storage of snow, the input of said fourth memory unit being connected to the output of the second multiplier.

Owing to the provision of a soil background gamma-quantum radiation detector, the device according to the invention for measuring moisture content of soil and snow water storage makes it possible to take into account the influence of hydrogen available in humus on readings of the cosmic-ray neutron detector placed deep in the soil so as to enhance accuracy of measurements in carrying out independent measurements of moisture content and water storage.

The above described pattern of relative positions of the three neutron detectors and two gamma-quantum detectors in the device according to the invention allows moisture content of soil and snow water storage to be determined simultaneously and independently taking into account biomass of a vegetation layer and humus of the soil.

When the detector of cosmic-ray neutrons passed through the snow layer is mounted with its base made of a hydrogen-containing material on the soil, moisture content of the soil cannot have any effect on readings of this detector because of the screening of albedo neutrons from the soil by the base of a hydrogen-containing material and by the snow layer. Although the snow water storage has a certain effect on readings of the detector of cosmic-ray neutrons passed through the soil, the ratio of readings of the detector of cosmic-ray neutrons passed through the soil to readings of the auxiliary detector of cosmic-ray neutrons passed through the snow layer having a base made of a hydrogen-containing material will only depend on moisture content of the soil so that moisture content of the soil can be determined with high accuracy. The snow water storage value is determined from readings of the detector of cosmic-ray neutrons passed through snow layer having a base of a hydrogen-containing material.

In this manner, simultaneous and independent measurement of snow water storage and soil moisture content is ensured. In order to carry out measurements of neutron flux which is influenced upon by moisture content of soil and snow water storage within volumes being monitored, all the three cosmic-ray neutron detectors must be positioned at a distance from one another that does not exceed path length of thermal neutrons before absorption in the atmosphere.

Readings of the device for measuring soil moisture content and snow water storage having the first detector of cosmic-ray neutrons passed through the soil are influenced by humus of the soil and biomass of the vegetation layer, and readings of the auxiliary detector of cosmic-ray neutrons passed through the snow layer are influenced by biomass of the vegetation layer. Accuracy of measurements is enhanced by taking into account influence of humus of the soil and biomass of the vegetation layer on intensity of cosmic-ray neutrons. To correct readings of the first detector of cosmic-ray neutrons passed through the soil and readings of the auxiliary detector of cosmic-ray neutrons passed through the snow layer, it is necessary to know content of humus in the soil and content of biomass in the vegetation layer.

Contents of humus in the soil and of biomass in the vegetation layer are measured by soil and vegetation layer background gamma-quantum radiation detectors, respectively. The soil background gamma-quantum radiation detector is placed on the soil surface and is spaced from the first cosmic-ray neutron detector at a distance which is not greater than the gamma-quantum path length in the soil so as to measure content of humus in the soil which influences readings of the first detector of cosmic-ray neutrons passed through the soil. The auxiliary vegetation layer background gamma-quantum radiation detector is placed on the soil surface and is spaced from the auxiliary cosmic-ray neutron detector at a distance which is not greater than the gamma-quantum path length in vegetation layer so as to measure biomass of this layer which influence readings of the auxiliary detector of cosmic-ray neutrons passed through the snow layer.

BRIEF DESCRIPTION OF THE DRAWINGS

The invention will now be described with reference to specific embodiments illustrated in the accompanying drawings, in which.

DETAILED DESCRIPTION OF THE INVENTION

Figure 1:
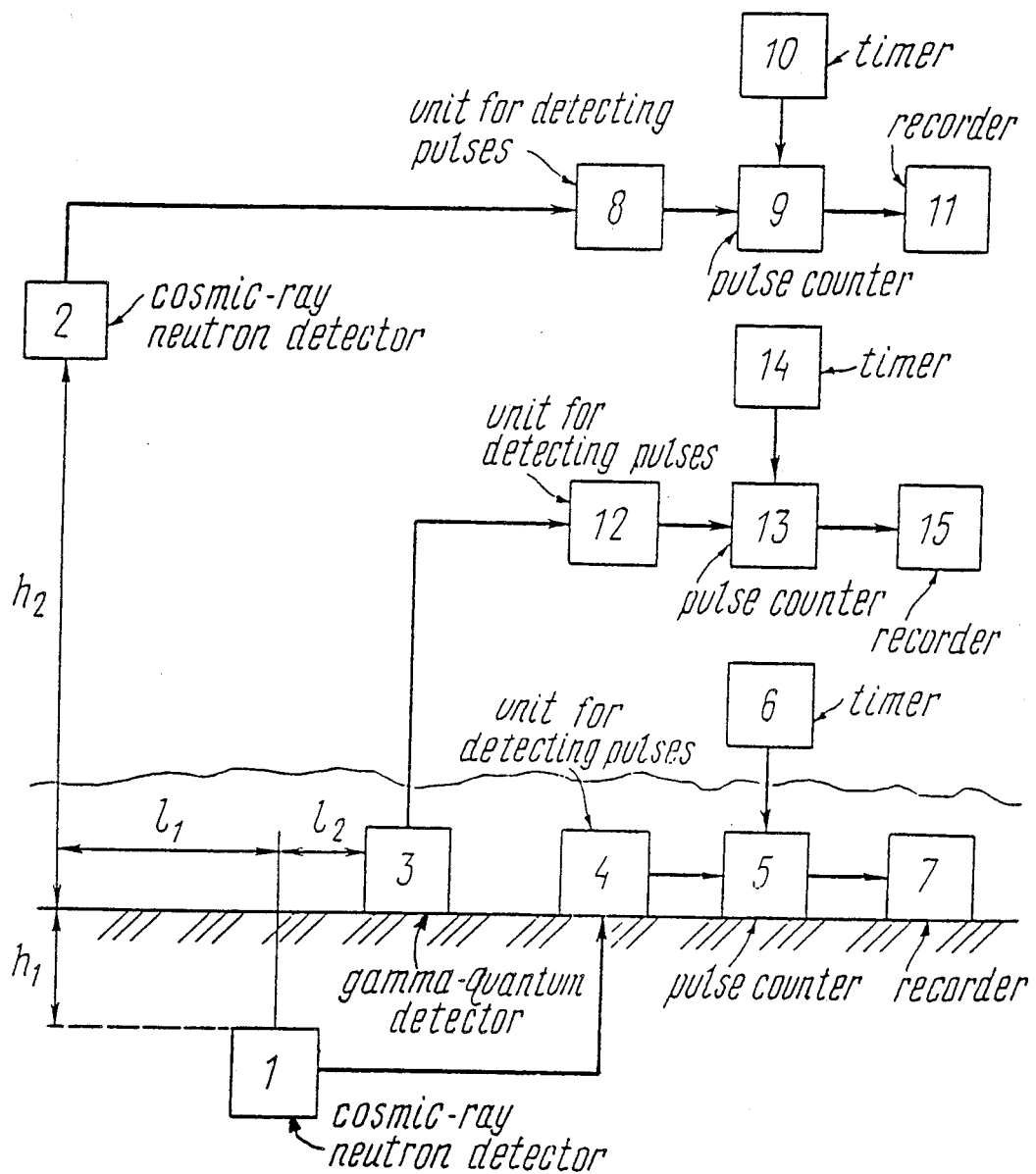
FIG. 1 is a block diagram of a device for measuring moisture content of soil and snow water storage taking into account humus of the soil, having one detector placed deep in the soil, a second detector placed above the soil, and a third detector placed on the soil surface, according to the invention.

A device for measuring moisture content of soil and snow water storage comprises a first detector 1 of cosmic-ray neutrons passed through the soil (FIG. 1) which is placed at a predetermined depth $h_1$ deep in the soil. The depth $h_1$ is determined by specific tasks depending on the field of use of the device. Thus, for the purposes of reclamation, the depth $h_1$ is determined by the depth of the root system of a crop (20 cm for cereals, 2–5 m for fruit trees). A second cosmic-ray neutron detector 2 is placed above the soil, at an altitude of $h_2$ which is greater than maximum thickness of snow pack or height of a vegetation layer(shown with wavy line in the drawing)and is spaced from the first cosmic-ray neutron detector 1 at a distance $l_1$ which is not greater than the path length of thermal neutrons before absorption in the atmosphere. The second cosmic-ray neutron detector 2 is designed for recording direct flux of neutrons in the atmosphere. A gamma-radiation detector which is referred to herebelow as soil background gamma-quantum detector 3 is placed on the soil surface and is spaced from the first cosmic-ray neutron detector at a distance $l_2$ which is not greater than the gamma-quantum path length before absorption in the soil so as to measure density of humus influencing readings of the first cosmic-ray neutron detector 1. The detector 1 is electrically coupled to a series circuit including a pulse detector unit 4 for detecting pulses of a predetermined amplitude and a pulse counter 5 having a control input to which is connected a timer 6 and an output connected to a recorder 7. The detector 2 is electrically coupled to a series circuit including a pulse detector unit 8 for detecting pulses of a predetermined amplitude and a pulse counter 9 having a control input to which is connected a timer 10 and an output connected to a recorder 11.

The soil background gamma-quantum radiation detector 3 is electrically coupled to a series circuit including a pulse detector unit 12 for detecting pulses of a predetermined amplitude and a pulse counter 13 having a control input to which is connected a timer 14 and an output connected to a recorder 15.

For measuring moisture content of soil and snow water storage taking into account humus of the soil and biomass of the vegetation layer, the device comprises a detector 16 (FIG. 2) of cosmic-ray neutrons passed through the snow layer, having a base 17 made of a hydrogen-containing material, e.g. polyethylene ($CH_2$), which is mounted with this base 17 on the soil surface and spaced at a distance $l_3$, $l_4$, respectively, from the first and second cosmic-ray neutron detectors 1, 2 which is not greater than the path length of thermal neutrons before absorption in the atmosphere. A gamma-radiation detector, referred to herebelow as vegetation layer background gamma-quantum radiation detector 18, placed on the soil layer and spaced from the cosmic-ray neutron detector 16 at a distance $l_5$ which is not greater than the gamma-quantum path length before absorption in the vegetation layer. The cosmic-ray neutron detector 16, similarly to the embodiment of the device shown in FIG. 1, is electrically coupled to a series circuit including a pulse detector unit 19 for detecting pulses of a predetermined amplitude and a pulse counter 20 having a control input to which is connected a timer 21 and an output connected to a recorder 22. The vegetation layer background gamma-quantum radiation detector 18 is electrically coupled to a series circuit including a pulse detector unit 23 for detecting pulses of a predetermined amplitude and a pulse counter 24 having a control input to which is connected a timer 25 and an output connected to a recorder 26.

For automatic processing of the results of measurements, the device for measuring the moisture content is additionally provided with the following units connected in series: a divider 27 (FIG. 3) producing output electric signals corresponding to the relative intensities of the cosmic-ray neutrons, passed through the soil and snow, and background gamma-quantum radiation from the soil and vegetation layer, the inputs of said divider being connected to the outputs of the pulse counters 5, 9, 13, 20 and 24 (in the embodiment being described said inputs are directly connected to said outputs), and a nonlinear converter 28 converting the electric signals corresponding to the relative intensities of the cosmic-ray neutrons passed through the soil and snow layer and the background gamma-quantum radiation from the soil and vegetation layer into electric signals corresponding to the moisture content of the soil and water storage of snow. The recorders 7, 11, 15, 22 and 26 (FIG. 2) are united into a common recorder 29 (FIG. 3), the outputs of the nonlinear converter 28 being connected to the inputs of the common recorder 29.

In the embodiment herein described the divider 27 comprises dividers 30, 31, 32 and 33. The input 34 of the divider 30 is a first input of the divider 27 and receives an electric signal corresponding to the intensity of the cosmic-ray neutrons passed through the soil, while the input 35 is a second input of the divider 27 and receives an electric signal corresponding to the intensity of the cosmic-ray neutrons passed through the snow layer, the divider 30 dividing the signal applied to the input 34 into a signal fed to the input 35. The input 36 of the divider 31 is connected to the input 35 of the divider 30, while the input 37 serves as a third input of the divider 27 and receives an electric signal corresponding to the intensity of the direct flow of cosmic-ray neutrons; divider 31 divides the signal applied to the input 36 into signal fed to the input 37. The input 38 of the divider 32 serves as a fourth input of the divider 27 and receives an electric signal corresponding to the intensity of background gamma-quantum radiation from the soil and the input 39 is connected to the input 37 of the divider 31, the divider 32 dividing the signal applied to the input 38 into signal fed to the input 39. The input 40 of the divider 33 is a fifth input of the divider 27 and receives an electric signal corresponding to the intensity of the background gamma-quantum radiation from the vegetation layer and the input 41 is connected to the input 39 of the divider 32, the divider 32 dividing the signal applied to the input 40 into signal fed to the input 40.

In the embodiment described the nonlinear converter 28 comprises a first memory unit 42 storing calibration dependence of the intensity of the cosmic-ray radiation passed through the soil on the soil humus; the input of the memory unit 42 serves as a first input of the nonlinear converter 28 and receives a signal from the divider 32, while the output is connected to the input 43 of the multiplier 44, whose input 45 is a second input of the nonlinear converter 28 and receives the signal from the output of the divider 30.

The nonlinear converter 28 also comprises a second memory unit 46 storing calibration dependence of intensity of the cosmic-ray neutrons passed through the vegetation layer of its biomass; the input of this unit 46 is a third input of the nonlinear converter 28 and receives a signal from the divider 33, while the output is connected to the input 47 of a multiplier 48, whose input 49 is a fourth input of the nonlinear converter 28 and receives a signal from the output of the divider 31.

The output of the multiplier 44 is connected to the input of a memory unit 50 storing calibration dependence of the humus-corrected relative intensity of the comsic-ray neutrons passed through the soil on the soil moisture content, the output of said memory unit 50 being an output of the nonlinear converter 28. The output of the multiplier 48 is connected to the input of a memory unit 51 storing calibration dependence of the humus-corrected relative intensity of the cosmic-ray neutron passed through the snow layer 28.

This embodiment of the device allows moisture content and snow water storage to be measured simultaneously, but it calls for taking readings from the recorders 7, 11, 15, 22, 26 (FIG. 2) and 29 (FIG. 3) by the operator directly on the site. It is not always convenient, and there are applications where the site of monitoring is hard to access for regular collection of data. Accordingly, the device according to the invention may be in a form allowing a remote data transmission to be carried out. For that purpose the device has a data accumulation, storage and transmission unit, 52 (FIG. 4) with pulse counters 5, 9, 13, 20 and 24 having their outputs connected to a common recorder 53 and control inputs connected to a common timer 54. In this embodiment, the recorder 53 has a shift register 55 having its data inputs connected to the outputs of the pulse counters 5, 9, 13, 20, 24 and a control input to an output of a control flip-flop 56 which is also connected to inputs of a clock counter 57 and a line counter 58.

The timer 54 is also connected to triggering inputs of the control flip-flop 56, clock counter 57 and line counter 58. A clock output of the timer 54 is connected to a count input of the line counter 58 having an output connected to an input of a frequency modulator 59 having its data input connected to an output of the shift register 55 and a clock input connected to the clock output of the timer 54. The output of the clock counter 57 is connected to a reset input of the control flip-flop 56. An output of the frequency modulator 59 which is the output of the recorder 53 and of the data accumulation, storage and transmission unit 52 is connected to a radio station. A receiver center 61 comprises a radio station 62 having an output connected to an input of an arithmetic and logic device 63 having its output connected to an input of a divider 27. An input-output of the non-linear converter 28 is connected to an input-output of a data input-output device 64, e.g. a display, and a data output is connected to an external data carrier 65.

The cosmic-ray neutron detectors 1, 2, 16 and background gamma-quantum radiation detectors 3, 18 are of a conventional type. Thus, each of the first and third cosmic-ray neutron detectors 1, 16 consists of a neutron counter surrounded by a layer of a hydrogen-containing material with a mass thickness in $g/cm^2$ chosen in such a manner as to achieve maximum sensitivity of the neutron counter. The detector 16 has the base 17 of a hydrogen-containing material with a mass thickness chosen to ensure reflection of albedo neutrons of the soil therefrom.

The second cosmic-ray neutron detector 2 consists of a neutron counter surrounded by three layers. The first layer, which follows the neutron counter, is a neutron decelerator and is made similarly to that described above. The second layer, which is a neutron generator, is made of lead with a thickness chosen to obtain a maximum number of generated neutrons. The third layer, which is a reflector, is made of a hydrogen-containing material with a thickness chosen to ensure reflection of the generated neutrons towards the counter and minimum sensitivity towards albedo neutrons from the soil and to low-energy neutrons from the atmosphere.

The soil background gamma-quantum radiation detector 3 is of a conventional type and is placed in a lead collimator oriented vertically downwardly so as to eliminate influence of biomass of vegetation layer on readings of the gamma-quantum detector 3.

The background vegetation layer gamma-quantum radiation detector 18 is similar to the detector 3 and is placed in a lead collimator oriented vertically upwardly so as to eliminate influence of soil humus on readings of the gamma-quantum detector 18.

The device for measuring moisture content of soil and snow water storage functions in the following manner.

The cosmic-ray neutron detector 1 (FIG. 1) placed in the soil at a depth $h_1$ records cosmic-ray neutrons passed through the soil. At the same time, the detector 2 placed at an altitude $h_2$ above the soil records direct flux neutrons of the atmosphere, i.e. records fluctuations of the primary comsic-ray flux that do not depend on moisture content of the soil, snow water storage, humus of soil and biomass of the vegetation layer. The soil background gamma-quantum radiation detector 3, simultaneously with the detectors 1, 2, records gamma-quantum radiation of carbon on the soil humus when acted upon by cosmic-rays. Pulses from the outputs of the detectors 1, 2, 3 go to the inputs of the respective units 4, 8, 12 for detecting pulses of a predetermined amplitude. The units 4, 8 for detecting pulses of a predetermined amplitude let through only pulses that correspond to cosmic-ray neutrons and do not let through pulses of lower amplitudes caused by actuation of the detectors 1, 2, in response to gamma-quantum radiation, electrons and muons. Accordingly, the unit 12 for detecting pulses does not let through pulses caused by actuation of the gamma-quantum detector 3 in response to the action of cosmic-rays upon soil components, except for carbon. Pulses from the outputs of the units 4, 8, 12 for detecting pulses go to the inputs of the pulse counters 5, 9, 13, respectively. The exposure time of the counters 5, 9, 13 is set-up by the timers 6, 10, 14. Sums of pulses from the detectors 1, 2, 3 are recorded by the respective recorders 7, 11, 15.

The measured sums of pulses from the detectors 1, 2, 3 are used to determine intensities $I_1$, $I_2$ of cosmic-ray neutrons and intensity $I_3$ of background gamma-quantum radiation during the exposure time. Moisture content W of soil taking into account humus is determined without snow pack using theoretically and experimentally obtained calibration relationships of relative intensity $I_1/I_2$ versus soil moisture content W and relative intensity $I_3/I_2$ versus soil humus G and a correction factor $K_g$ taking into account influence of humus G on intensity $I_1$.

Snow water storage P is determined by the resultant ratio $I_1/I_2$ using theoretical and experimental calibration relationships of relative intensity $I_1/I_2$ versus snow water storage P.

Figure 2:
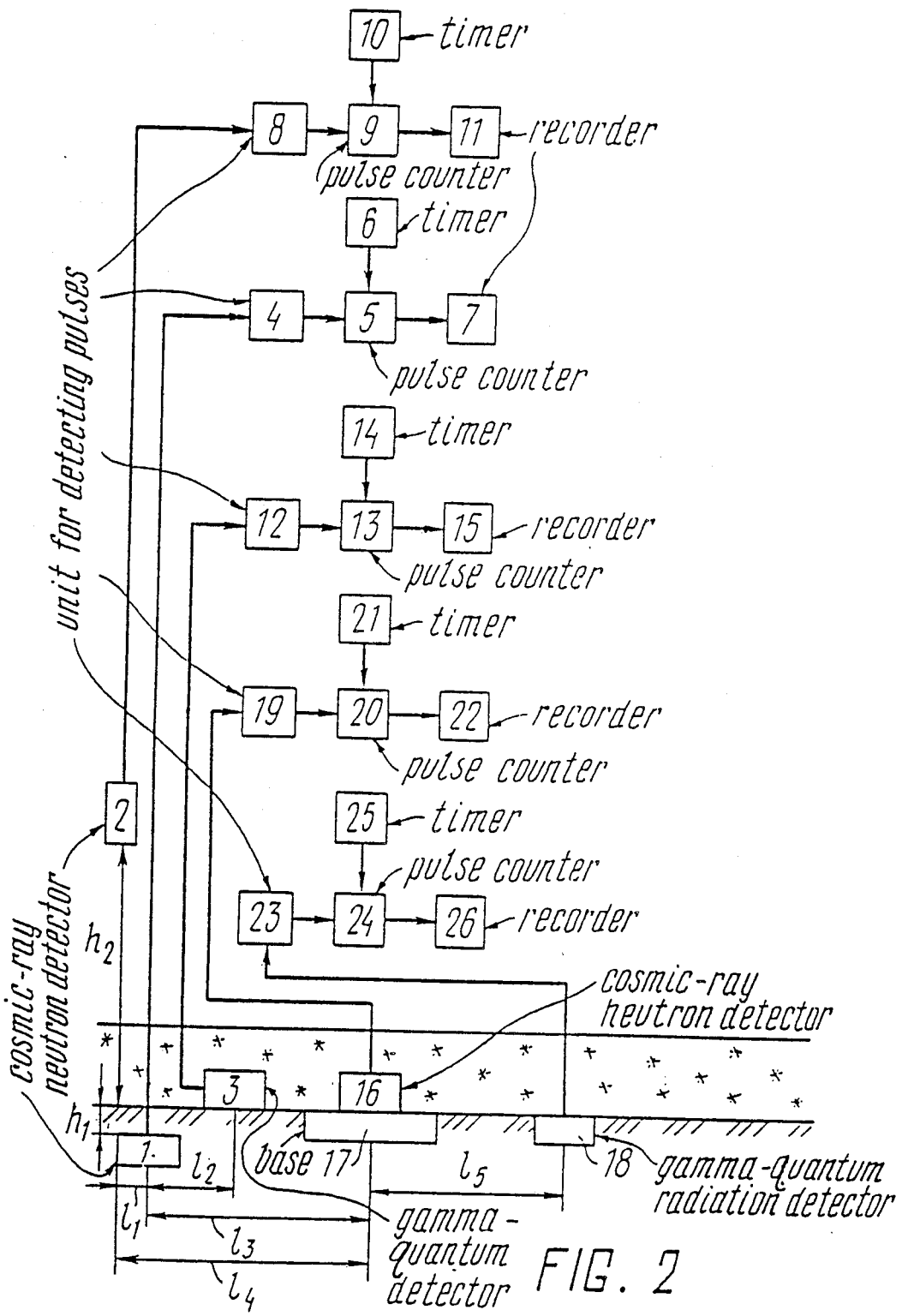
FIG. 2 is a block diagram of the device shown in of FIG. 1, for taking into account influence of biomass of a vegetation layer, according to the invention.

Operation of the device in the embodiment illustrated in FIG. 2 is similar to that described above. The only difference is that the cosmic-ray neutron detector 16 (FIG. 2) having the hydrogen-containing base 17 records cosmic-ray neutrons passed through the snow layer. The vegetation layer background gamma-quantum radiation detector 18 records, simultaneously with the detectors 1, 2, 3, 16, gamma-quantum radiation of carbon of the biomass of vegetation when acted upon by cosmic-rays. Pulses from the ouputs of the detectors 16, 18 arrive at the inputs of the units 19, 23 for detecting pulses of a predetermined amplitude, respectively. The unit 19 lets through pulses corresponding to cosmic-ray neutrons only and does not let through lower-amplitude pulses caused by actuation of the detector 16 in response to gamma-quantum radiation, electrons and muons. The unit 23 for detecting pulses lets through pulses caused by actuation of the detector 18 only in response to gamma-quantum radiation caused by action of cosmic-rays upon carbon of the vegetation layer. Pulses from the outputs of the units 19, 23 for detecting pulses arrive at the inputs of the pulse counters 20, 24, respectively. The exposure time of the counters 20, 24 is set-up by the timers 21, 25. Sums of pulses from the detectors 16, 18 are recorded by the recorders 22, 26, respectively.

The measured sums of pulses from the detectors 16, 18 are used for determining intensity $I_{16}$ of cosmic-ray neutrons and intensity $I_{18}$ of gamma-quantum radiation during the exposure time. Snow water storage P is determined taking into account biomass Q of the vegetation layer using the oretically and experimentally obtained calibration relationships of relative intensity $I_{16}/I_2$ versus snow water storage P and relative intensity $I_{18}/I_2$ versus biomass Q of the vegetation layer and a correction factor $K_b$ taking into account influence of biomass Q on intensity $I_{16}$.

Moisture content W of soil taking into account soil humus G in the presence of snow pack is determined using the oretically and experimentally obtained calibrations relationships of relative intensity $I_1/I_{16}$ versus soil moisture content W and relative intensity $I_3/I_2$ versus soil humus G and a correction factor $K_g$ taking into account influence of humus G on intensity $I_1$.

Figure 3:
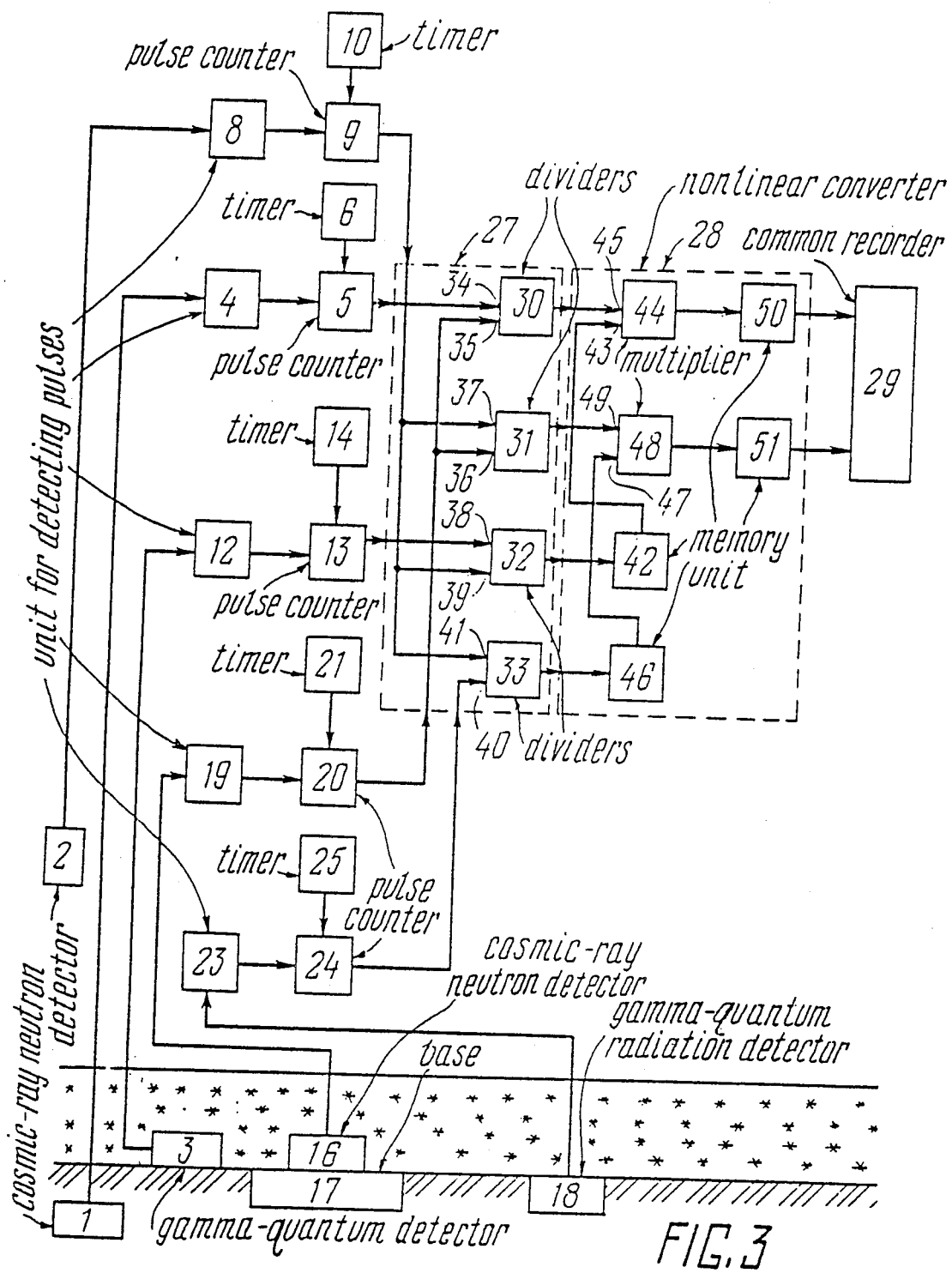
FIG. 3 is a block diagram of the device shown in FIG. 2, with automatic data processing, according to the invention.
Figure 4:
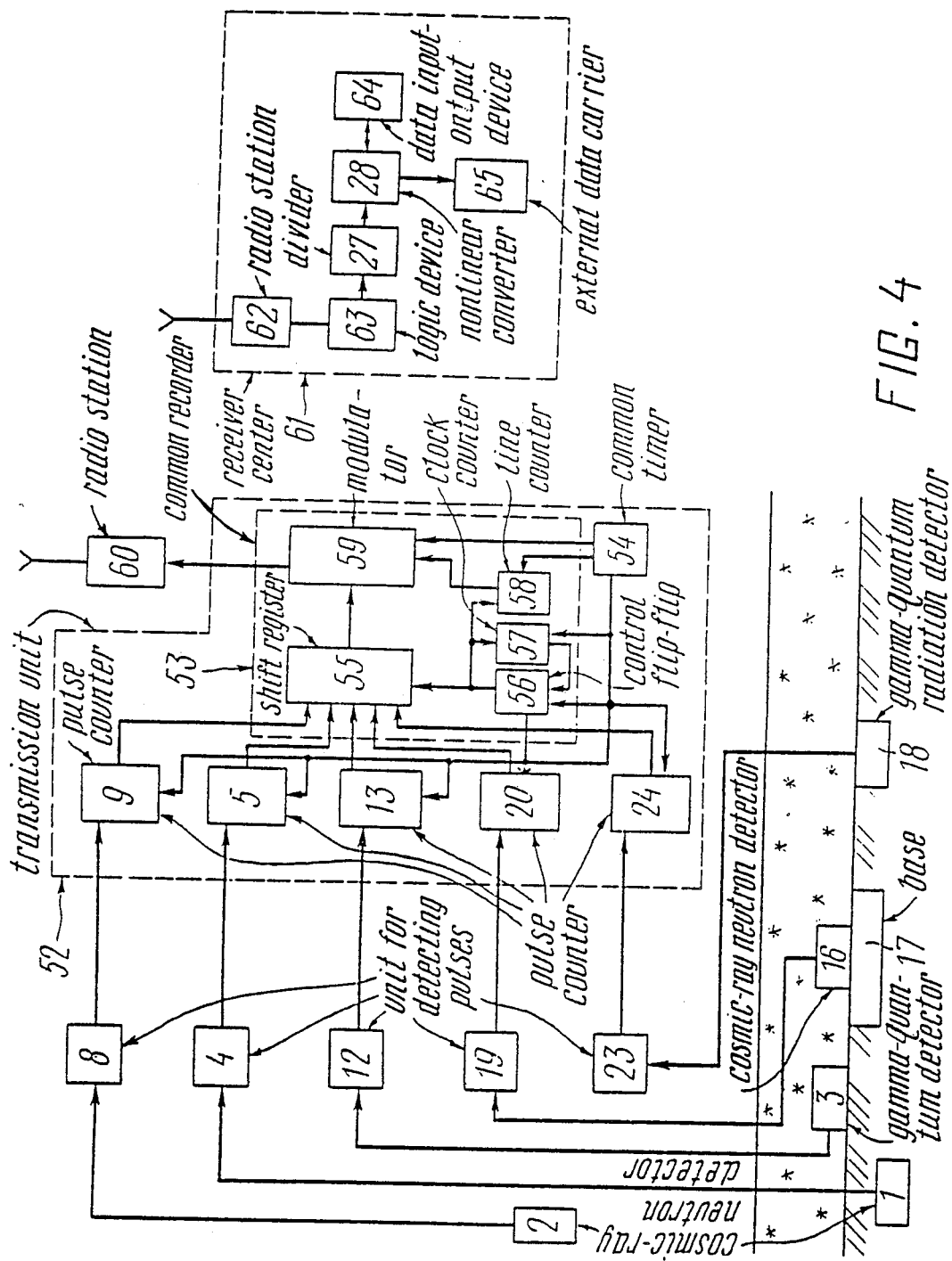
FIG. 4 is a block diagram of the device shown in FIG. 2, with remote data transmission.

The operation of the device shown in FIG. 3 is essentially the same as described above. The difference consists in that the measured intensities $I_1$, $I_{16}$, $I_2$, $I_8$, $I_{18}$ applied respectively to the first, second, third, fourth and fifth inputs of the divider 27 in the form of electric signals are used for measuring the intensity $I_1/I_{16}$. $I_{16}/I_2$ of the cosmic-ray neutron passed through the soil and snow layer, and the relative intensity $I_3/I_2$, $I_{18}/I_2$ of the background gamma-quantum radiation from the soil and vegetation layer, in dividers 30, 31, 32, 33. The relative intensities $I_3/I_2$, $I_1/I_{16}$, $I_{18}/I_2$, $I_{16}/I_2$ applied respectively to the first, second, third and fourth inputs of the nonlinear converter 28 are used for determining the soil moisture W and water storage P of snow. The memory unit 42 of the nonlinear converter 28 is used for conversion of the relative intensity $I_3/I_2$ into a correction factor $K_g$, which is then fed into the multiplier 44 where it is multiplied by the relative intensity $I_1/I_{16}$. The memory unit 50 of the nonlinear converter 28 is used for conversion of the product $K_g I_1/I_{16}$ into the soil moisture W. The memory unit 46 of the nonlinear converter 28 is used for conversion of the relative intensity $I_{18}/I_2$ into a correction factor $K_b$, which is then fed into the multiplier 48, where is multiplied by the relative intensity $I_{16}/I_2$. The obtained product $K_b I_{16}/I_2$ is fed into the memory unit of the nonlinear converter 28, where it is converted into water storage P of snow. The moisture W and water storage P are recorded in the common recorder 29.

With the remote data transmission, pulses from the units 4, 8, 12, 19, 23 for detecting pulses go to the inputs of the pulse counters 5, 9, 13, 20, 24 of the data accumulation, storage and transmission unit 52 (FIG. 3). Following a "write" signal arriving from the timer 54, data from the outputs of the pulse counters 5, 9, 12, 13, 20, 24 is loaded into the shift register 55. Data from the output of the shift register 55 is fed to the input of the frequency modulator 59. The frequency modulator 59 is in the form of a divider with a variable division ratio. The division ratio depends on signals arriving at the input of the frequency modulator 59. The initial frequency is the frequency of a quartz oscillator 32,768 Hz fed from the output of the timer 54. Signals at the frequency 32,768 Hz are fed from the output of the timer 54 to the input of the frequency modulator 59, signals at the frequency 2 Hz are fed to the input of the line counter 58, and a signal corresponding to a preset exposure time is fed to the triggering input of the control flip-flop 56.

The "write" signal triggers the unit 52 to the data transmission mode, i.e. the control flip-flop 56 is set to permit operation of the clock counter 57 and line counter 58. The clock counter 57 is designed for counting data shift clocks and is in the form of a divider.

To enhance reliability of data transmission, there is provided a four-fold repetition of data transmission. Remote data transmission is carried out through radio channels by means of the radio station 60 connected to the frequency modulator 59. Data is received at the receiving center 61.

The data is processed in the receiving center 61 in the following manner. After reception by the radio station 62, the ratios $I_{16}/I_2$, $I_1/I_{16}$, $I_3/I_2$, $I_{18}/I_2$, $K_g I_1/I_{16}$, $K_b I_{16}/I_2$ are determined in the arithmetic and logic device 27 to be then converted in the non-linear converter 28 in accordance with the abovementioned calibration relationships of the snow water storage P, soil moisture content W, humus G and biomass Q. The data is put out to the input-output device 64 and to the external data carrier 65.

Let us consider the influence of soil humus and vegetation layer biomass on measurements of soil moisture content and snow water storage. As shown by the analysis, the elemental composition of plants in air-dry state is as follows: carbon 45%, oxygen 42%, hydrogen 6.5%, nitrogen 4.5%, mineral elements 5%. Humus generally amounts to 80–90% of the total amount of organic matter available in soil. There is a correlation between content of carbon in humus and biomass and content of hydrogen.

Owing to the presence of hydrogen, soil humus and biomass of the vegetation layer influence the measured intensity of cosmic-ray neutrons.

The amount of hydrogen available in humus and biomass is known for a given content of humus and biomass. The amount of humus in the soil at a depth x can be approximately expressed by an exponential relationship of the following form: $A(x) = A_o \exp(-bx\rho)$, wherein $A_o$ is the volumetric concentration of humus on the soil surface with $x=0$, $\rho$ is the soil density; b is the coefficient determining the rate of decrease in humus with depth. The value of the coefficient b depends on the soil type and ranges from $10^{-2}$ cm$^{-1}$ for leached black soils to $3 \cdot 10^{-2}$ cm$^{-1}$ for podzolic soils. Humus storage $G(x_1)$ between the soil surface and a depth level $x_1$ is determined as follows:

$$G(x_1) = \int_0^{x_1} A(x)dx = A_o \int_0^{x_1} e^{-\beta x \rho} dx = \frac{A_o}{\beta \rho}(1 - e^{-\beta x_1 \rho}) \quad (1)$$

Owing to the correlation between humus storage and hydrogen content of humus, hydrogen storage $Hg(x_1)$ between the soil surface and a depth $x_1$ is determined as follows:

$$Hg(x_1) = c \cdot G(x_1), \quad (2)$$

wherein c is the coefficient characterizing relative weight content of hydrogen in humus.

The effective moisture content $W(x_1)$ of soil at depth $x_1$ is determined from the formula:

$$W(x_1) = Hg(x_1) + \rho \int_0^{x_1} W(x)dx \quad (3)$$

wherein
W(x) is the relative weight content of moisture in soil;
$\rho$ is the density of soil.
With W(x)=const $$W(x_1) = Hg(x_1) + W^*(x_1) \quad (4)$$

wherein
$W^x(x_1) = W \cdot x_1$.

With a pre-set moisture content of soil, intensity $I(x_1)$ of neutrons at a depth $x_1$ is determined as follows:

$$\tau(x_1) = \tau_o \exp(-\alpha_n \cdot x_1 \cdot \rho \cdot w), \quad (5)$$

wherein
$I_o = I_{x=o}$.

α is the neutron attenuation coefficient equal to $5.4 \cdot 10^{-3}$ cm$^2$/g.

With a pre-set humus content in soil, intensity of neutrons, as follows from formulae (4) and (5), is determined as follows:

$$\tau^1(x_1) = \tau_o \exp[-\alpha_n \cdot W(x_1)] \quad (6)$$

and diminished by the value of $\Delta I(x_1) = I(x_1) - I'(x_1)$.

The correction factor $K_g$ taking into account the presence of humus in the soil is determined as follows:

$$Kg(x) = \frac{\tau(x)}{\tau'(x)} = \exp[\alpha_n \cdot Hg(x)] \quad (7)$$

Therefore, measurement of humus in the soil makes it possible to make an unambiguous correction in the measurement of soil moisture content.

The correction factor $K_b$ taking into account the presence of biomass of the vegetation layer in measuring snow water storage is determined in the similar manner. It should be, however, borne in mind that with a certain hydrogen content of the biomass, water storage of a substance increases on the account of moisture content of the plants proper. There is a correlation between carbon storage and moisture content of plants for supporting their normal life. Therefore, if biomass of the plants is measured, hydrogen storage $H_b$ in the plants may be determined so as to make the correction in the measurements of soil moisture content and snow water storage using the formula:

$$K\beta = \exp(\alpha_n \cdot H\beta) \quad (8)$$

Figure 5B:
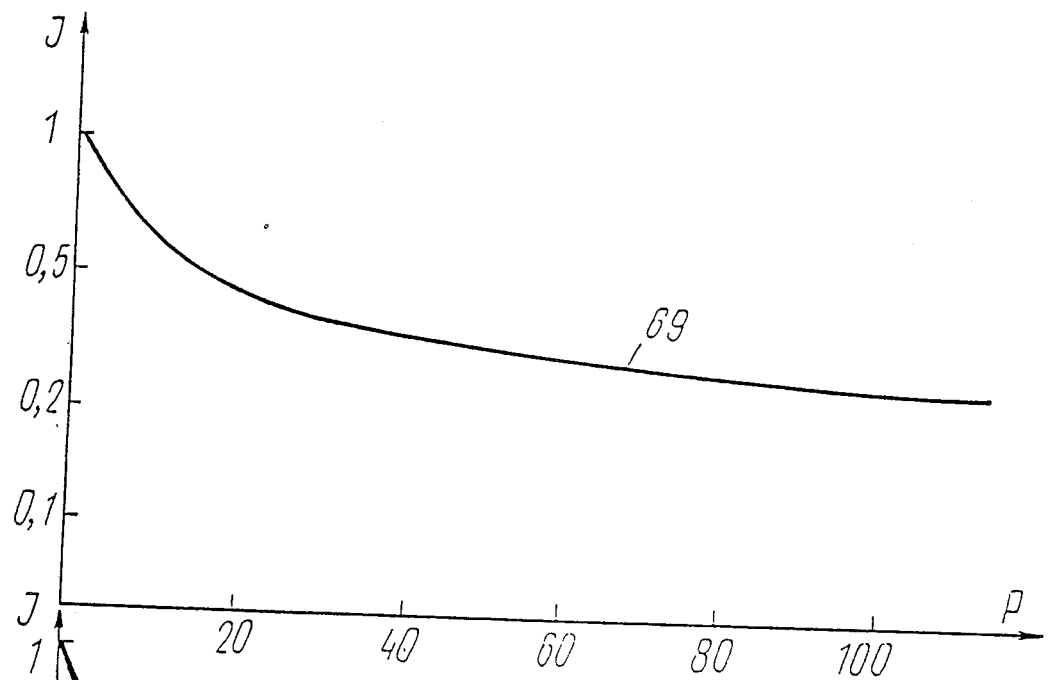
FIG. 5($a$, $b$) shows graphs of the relationship of intensity of cosmic-ray neutrons versus soil moisture content and snow water storage at different depths in the soil.
Figure 5A:
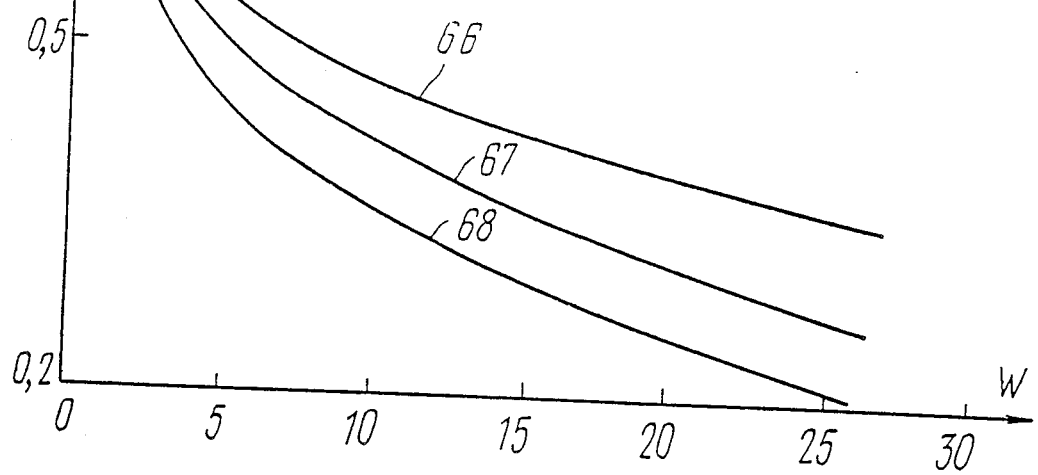

For a better understanding of operation of the device for measuring soil moisture content and snow water storage, FIG. 5a shows a diagram of relationship of intensity of cosmic-ray neutrons I in relative units plotted on the ordinates versus soil moisture content W in % plotted on the abscissa, in the form of a curve 66 for a depth of installation of the neutron detector in the soil corresponding to soil density $\rho = 10$ g/cm$^2$, a curve 67 for a depth corresponding to soil density $\rho = 50$ g/cm$^2$ and a curve 68 for a depth corresponding to soil density $\rho = 80$ g/cm$^2$, and FIG. 5b shows a diagram of intensity of cosmic-ray neutrons I in relative units plotted on the ordinates versus snow water storage P in g/cm$^2$ plotted on the abscissa, in the form of a curve 69.

EXAMPLE

The detector 1 was placed in the soil at a depth $x_1$ corresponding to $\rho = 50$ g/cm$^2$; b=0.015 for this soil. Then $$Hg(x_1) = \frac{A_o}{\beta \cdot \rho} [1 - \exp(-x_1 \cdot \beta \cdot \rho)].$$

The value of $A_o$ is determined from the formula $A_o = (0.1 - 0.15)\rho$. If $\rho = 1.5$ g/cm$^3$ and $A_o = 0.15\rho$, obtain $Hg(x_1) \approx 53$ g/cm$^2$. Then $K_g(x_1) \approx 1.33$. With $I_1/I_{16} = 0.3$, soil moisture content W is 19% from the curve 67 (FIG. 5a). With correction of $I_1/I_{16}$ by $K_g(x_1)$, $I_1/I_{16} = 0.4$ and W=9.5%.

Let us consider the case when biomass of the vegetation layer is taken into account and when its uniform density is $\rho = 1$ g/cm$^3$. The weight content of hydrogen is about 50% according to the formula $H_b = Q/2$. For the height of the vegetation layer h=100 cm, $H_b = 50$ g/cm$_2$. From (8), $K_g \approx 1.31$.

If $I_{16}/I_2 = 0.3$, snow water storage P is 10 cm of water equivalent according to the curve 69 (FIG. 5b). With the correction of $I_{16}/I_2$ by $K_b$, $I_{16}/I_2 = 0.4$ and P=8 cm of water equivalent.

Therefore, the device for measuring moisture content of soil and snow water storage is capable of simultaneously and independently carrying out the determination of soil moisture content and snow water storage taking into account soil humus and biomass of vegetation layer, with high accuracy.

We claim:

1. A device for measuring moisture content of soil and snow water storage, said device comprising:
   a first cosmic-ray neutron detector comprising means for recording cosmic-ray neutrons passed through the soil at a pre-set depth and an output;
   a second cosmic-ray neutron detector comprising means for recording direct flux of neutrons in the atmosphere at an altitude which is greater than maximum snow pack thickness or height of a vegetation layer and an output, said second cosmic-ray neutron detector being displaced from said first cosmic-ray neutron detector at a distance which is not greater than path length of thermal neutrons before absorption in the atmosphere;
   a first gamma-radiation detector comprising means for recording soil background gamma-quantum radiation on the soil surface, and an output, said first gamma-radiation detector being displaced from said first cosmic-ray neutron detector at a distance which is not greater than gamma-quantum path length before absorption in the soil;
   first and second units for detecting pulses of a predetermined amplitude, each having an input and an output, said inputs of said first and second units for detecting pulses of a predetermined amplitude being respectively electrically coupled to said outputs of said first and second cosmic-ray neutron detectors, said first and second units for detecting pulses of a predetermined amplitude being designed for letting through only pulses corresponding to cosmic-ray neutrons passed through the soil and direct neutron flux of the atmosphere;
   a third unit for detecting pulses of a predetermined amplitude having an input and an output, said input of said third unit for detecting pulses of a predetermined amplitude being electrically coupled to said output of said first gamma-radiation detector, said third unit for detecting pulses of a predetermined amplitude being designed for letting through only pulses corresponding to soil background gamma-quantum radiation;
   first, second and third pulse counters, each having an input, a control input and an output, said inputs of said first, second and third pulse counters being respectively connected to said outputs of said first, second and third units for detecting pulses of a predetermined amplitude, said first, second and third pulse counters being designed for counting pulses corresponding to cosmic-ray neutrons passed through the soil, pulses corresponding to the direct neutron flux of the atmosphere and pulses corresponding to soil background gamma-quantum radiation during a pre-set exposure time;
   first, second and third timers, each having an output connected to said control input of a respective pulse counter, said first, second and third timers being designed for setting-up the exposure time of said first, second and third pulse counters; and first, second and third recorders, each having an input connected to said output of a respective pulse counter, said first, second and third recorders being designed for recording pulses corresponding to the total number of cosmic-ray neutrons passed through the soil, direct neutron flux of the atmosphere and soil background gamma-quantum radiation during the exposure time.

2. A device for measuring moisture content of soil according to claim 1, said device further comprising:

a third cosmic-ray neutron detector comprising means for recording cosmic-ray neutrons passed through the snow layer, an output, and a base made of a hydrogen-containing material, said third cosmic-ray neutron detector being displaced from said first and second cosmic-ray detectors at a distance which is not greater than path length of thermal neutrons before absorption in the atmosphere;

a second gamma-radiation detector comprising means for recording the vegetation layer background gamma-quantum radiation on the soil surface, and an output, said second gamma-radiation detector being displaced from said third cosmic-ray neutron detector at a distance which is not greater than gamma-quantum path length before absorption in a vegetation layer;

fourth and fifth units for detecting pulses of a predetermined amplitude, each having an input and an output, said inputs of said fourth and fifth units for detecting pulses of a predetermined amplitude being electrically coupled to said outputs of said third cosmic-ray neutron detector and second gamma-radiation detector, respectively, said fourth and fifth units for detecting pulses of a predetermined amplitude being designed for letting through only pulses corresponding to cosmic-ray neutron detectors passed through the snow layer and pulses corresponding to the vegetation layer background gamma-quantum radiation;

fourth and fifth pulse counters, each having an input, a control input and an output, said inputs of said fourth and fifth pulse counters being connected to said outputs of said fourth and fifth units for detecting pulses of a predetermined amplitude, respectively, said fourth and fifth pulse counters being designed for counting pulses corresponding to cosmic-ray neutrons passed through the snow layer and pulses corresponding to the vegetation layer background gamma-quantum radiation during a pre-set exposure time;

fourth and fifth timers, each having an output, said outputs of said fourth and fifth timers being connected to said control inputs of said fourth and fifth pulse counters, respectively, said fourth and fifth timers being designed for setting-up the exposure time; and fourth and fifth recorders, each having an input, said inputs of said fourth and fifth recorders being connected to said outputs of said fourth and fifth pulse counters, respectively, said fourth and fifth recorders being designed for recording pulses corresponding to a total number of cosmic-ray neutrons passed through the snow layer and the vegetation layer background gamma-quantum radiation.

3. A device for measuring the moisture content of soil according to claim 2, further comprising:

a divider having a group inputs and a group of outputs, said divider being connected through said inputs of said group of inputs of said divider to said outputs of the first, third, fourth and fifth pulse counters and comprising means for division of the electric signals corresponding to the intensity of the cosmic-ray neutrons passed through the soil and snow layer into an electric signal corresponding to the intensity of the direct flow of neutrons of the atmosphere, an electric signal corresponding to the intensity of background gamma-quantum radiation from the soil, and electric signal corresponding to the intensity of the direct flow of neutrons of the atmosphere, and an electric signal corresponding to the intensity of the direct flow of neutrons of the atmosphere; and a nonlinear converter comprising means for converting the electric signals corresponding to the relative intensities of the cosmic-ray neutrons passed through the soil and snow layer and background gamma-quantum radiation from the soil into electric signals corresponding to the moisture of soil and the water storage of snow, having a group of inputs, a first output and a second output, said group of inputs of said nonlinear converter being connected to said outputs of said divider; wherein said first, second, third, fourth and fifth recorders being united into a common recorder having a first input and a second input connected to said first and second outputs of said nonlinear converter and comprising means for recording the moisture of soil and the water storage of snow.

4. A device for measuring moisture content of soil according to claim 3, in which said nonlinear converter includes:

a first memory unit storing calibration dependence of the intensity of the cosmic-ray neutron passed through the soil on the soil humus and having an input comprising means for receiving an electric signal corresponding to the relative intensity of the background gamma-quantum radiation from the soil, and having an output;

a first multiplier having a first input, a second input and an output, said first input of said first multiplier being connected to said output of said first memory unit, said second input of said first multiplier comprising means for receiving an electric signal corresponding to the relative intensity of the cosmic-ray neutrons passed through the soil;

a second memory unit storing the calibration dependence of the intensity of the cosmic-ray neutrons passed through the vegetation layer on its biomass, said second memory unit having an input comprising means for receiving an electric signal corresponding to the relative intensity of the background gamma-quantum radiation from the vegetation layer, and an output;

a second multiplier having a first input, a second input and an output, said first input of said second multiplier is connected to said output of said second memory unit, said second input of said second multiplier comprising means for receiving an electric signal corresponding to the relative intensities of the cosmic-ray neutrons passed through the snow layer;

a third memory unit storing calibration dependence of the humus-corrected relative intensity of the cosmic-ray neutrons passed through the soil on the soil moisture content, said third memory unit having an input and an output, said input of said third memory unit being connected to said output of said first multiplier; and a fourth memory unit storing calibration dependence of the humus-corrected relative intensity of the cosmic-ray neutrons passed through the snow layer on the water storage of snow, said fourth memory unit having an input and an output, said input of said fourth memory unit being connected to said output of said second multiplier; and wherein said outputs of said third and fourth memory unit serve as said first and second outputs of said nonlinear converter.

* * * * *